(12) United States Patent
Gonzalez et al.

(10) Patent No.: US 7,186,404 B2
(45) Date of Patent: *Mar. 6, 2007

(54) PHOTOSTABLE SUNSCREEN COMPOSITIONS AND METHODS OF STABILIZING

(75) Inventors: Anthony D. Gonzalez, Waldwick, NJ (US); Andrew H. Pechko, Ridgewood, NJ (US); Robert E. Kalafsky, Ogdensburg, NJ (US)

(73) Assignee: Avon Products, Inc., New York, NY (US)

( * ) Notice: Subject to any disclaimer, the term of this patent is extended or adjusted under 35 U.S.C. 154(b) by 3 days.

This patent is subject to a terminal disclaimer.

(21) Appl. No.: 11/093,217

(22) Filed: Mar. 29, 2005

(65) Prior Publication Data

US 2005/0186159 A1     Aug. 25, 2005

Related U.S. Application Data

(63) Continuation of application No. 10/226,757, filed on Aug. 23, 2002, now abandoned, which is a continuation-in-part of application No. 10/020,642, filed on Dec. 14, 2001, now Pat. No. 6,440,402.

(51) Int. Cl.
*A61Q 17/00* (2006.01)
*A61Q 17/04* (2006.01)
*A61Q 19/00* (2006.01)
*A61K 8/02* (2006.01)
*A61K 36/00* (2006.01)

(52) U.S. Cl. .................. 424/59; 424/60; 424/400; 424/401; 424/725; 424/773; 424/774; 424/775; 424/778; 424/779

(58) Field of Classification Search .................. 424/59, 424/60, 400, 401, 725, 773, 774, 775, 778, 424/779
See application file for complete search history.

(56) References Cited

U.S. PATENT DOCUMENTS

| | | | |
|---|---|---|---|
| 5,000,945 A | 3/1991 | Masahiro et al. | |
| 5,952,391 A | 9/1999 | Gers-Barlag et al. | |
| 5,985,251 A | 11/1999 | Gonzenbach et al. | |
| 6,048,516 A | 4/2000 | Bringhen et al. | |
| 6,071,501 A | 6/2000 | Robinson | |
| 6,180,119 B1 | 1/2001 | Boussouira et al. | |
| 6,210,658 B1 | 4/2001 | Bonda | |
| 6,338,838 B1 | 1/2002 | Berset et al. | |
| 6,372,237 B1 | 4/2002 | Boussouira et al. | |
| 6,440,402 B1 * | 8/2002 | Gonzalez et al. | 424/59 |

FOREIGN PATENT DOCUMENTS

| | | |
|---|---|---|
| DE | 19604580 | 8/1997 |
| JP | 61291515 A | 12/1986 |
| JP | 08157346 A | 6/1996 |
| JP | 09030948 A | 2/1997 |

OTHER PUBLICATIONS

"Naturally Occurring Isoamyl p-Methoxycinnamate," Langner et al., Cosmetics & Toiletries Magazine, vol. 112, Jan. 1997.
International Search Report, 3 pages.
"Naturlich vorkommender UV-Lichtschutzfilter: p-Methoxyzimtsaure-isoamylester," Langner et al., Parfumerie und Kosmetik, vol. 77, No. 5, May 1996.
"Composition of the essential oil of Rhizomes of Kaempferia galanga L" Wong et al. Chemical Abstracts & Indexs vol. 17, No. 118.
Supplemental European Search Report for EP Application No. 02766074.

* cited by examiner

*Primary Examiner*—Shelley A. Dodson
(74) *Attorney, Agent, or Firm*—Ohlandt, Greeley, Ruggiero & Perle, L.L.P.

(57) ABSTRACT

There is provided a photostable and synergistically enhanced topical sunscreen composition. There is further provided a method of enhancing the photostability of a sunscreen active in a topical sunscreen composition. There is further still provided a method of synergistically enhancing the UV absorbance of a sunscreen active in a topical sunscreen composition. The preferred compositions and methods of the present invention use a dibenzoylmethane sunscreen active, a *Kaempferia galanga* extract, and a cosmetically acceptable vehicle.

39 Claims, No Drawings

PHOTOSTABLE SUNSCREEN COMPOSITIONS AND METHODS OF STABILIZING

CROSS-REFERENCE TO A RELATED APPLICATION

This application is a continuation of U.S. Ser. No. 10/226,757, filed Aug. 23, 2002 now abandoned, which is a continuation-in-part application of U.S. Ser. No. 10/020,642, filed Dec. 14, 2001 now U.S. Pat. No. 6,440,402, both of which are incorporated herein by reference.

BACKGROUND OF THE INVENTION

1. Field of the Invention

The present invention relates to the use of *Kaempferia galanga* extract to photostabilize a topical sunscreen composition and synergistically enhance the UV absorbancy of a sunscreen composition. More particularly, the present invention relates to a sunscreen composition having a sunscreen active, particularly dibenzoylmethane and/or its derivatives, and an extract of *Kaempferia galanga*, particularly from the root thereof. The present invention also relates to a method of photostabilizing a sunscreen active in the topical sunscreen composition. The present invention further relates to a method of synergistically enhancing the UV absorbancy of a topical sunscreen composition having at least one sunscreen active.

2. Description of the Prior Art

Commercial sunscreen compositions commonly include at least one sunscreen active. To specifically protect against UV-A radiation, a UV-A sunscreen, such as a dibenzoylmethane derivative (e.g. butylmethoxydibenzoylmethane also known as avobenzone) is used to provide protection from UV-A radiation.

A common problem associated with some sunscreen compositions is a tendency of sunscreen actives, including dibenzoylmethane and/or derivatives thereof, to photodegrade over time from exposure to UV (ultraviolet) light. This results in a reduction of the UV absorbance of the composition, particularly UV-A absorbance, and, thus, a diminution in sunscreen protection for the user during extended exposure to sunlight.

U.S. Pat. No. 5,952,391 relates to sunscreen compositions having dibenzoylmethane sunscreen actives. The compositions have flavone or flavanone derivatives to stabilize the dibenzoylmethane actives.

An extract of *Kaempferia galanga* is disclosed in *Naturally Occurring Isoamyl p-Methoxycinnamate*, Cosmetics and Toiletries magazine, vol. 112, pp. 74–77, January 1997, which is incorporated herein by reference thereto. Topical compositions having the extract are disclosed in Japanese Application Nos. 8157346A2, 61291515A2, S61-291515 and 9030948A2. The extract has been disclosed as useful as a sunscreen, anti-inflammatory agent, skin lightening agent and food ingredient.

It would be desirable to have a sunscreen composition that is photostable and affords the claimed sunscreen protection for an extended period of time. It would be further desirable to have a photostable sunscreen composition that has a dibenzoylmethane and/or derivative thereof (hereafter collectively "dibenzoylmethane"). It would be still further desirable to have a photostable sunscreen composition that affords an enhanced degree of sunscreen protection.

SUMMARY OF THE INVENTION

It is an object of the present invention to provide a topical sunscreen composition having a photostable sunscreen active.

It is another object of the present invention to provide a topical sunscreen composition affording enhanced photostability for a dibenzoylmethane sunscreen active.

It is still another object of the present invention to provide a topical sunscreen composition that exhibits synergistic UV absorbance benefits upon prolonged exposure to sunlight.

These and other objects and advantages of the present invention are achieved by a topical sunscreen composition having a sunscreen active, a photostabilizing and/or UV absorbance enhancing amount of an extract of *Kaempferia galanga*, and a cosmetically acceptable vehicle.

There is also provided a method of enhancing the photostability of a sunscreen active in a topical sunscreen composition. An extract of *Kaempferia galanga* is introduced into the composition in an amount sufficient to enhance the photostability of the sunscreen active.

There is also provided a method of synergistically enhancing the UV absorbance of a topical sunscreen composition having a sunscreen active. An extract of *Kaempferia galanga* is introduced into the composition in an amount sufficient to synergistically enhance UV absorption.

DETAILED DESCRIPTION OF THE INVENTION

It was found surprising and unexpected that the photostability of a topical sunscreen composition having a sunscreen active, particularly dibenzoylmethane and/or derivatives thereof, could be enhanced by the introduction of an extract of *Kaempferia galanga*, particularly from the root thereof. It was also found surprising and unexpected that UV absorption capability of such a composition was synergistically enhanced by the introduction into the composition of the extract of *Kaempferia galanga*.

The present composition has one or more active sunscreens. Such sunscreen actives may be organic or inorganic and water-soluble or oil-soluble. Such actives include those for UVA and UVB protection (290 to 400 nanometer solar radiation). Such sunscreen actives include, but are not limited to, one or more of the following: dibenzoylmethane, oxybenzone, sulisobenzone, dioxybenzone, menthyl anthranilate, para aminobenzoic acid (PABA), octyl methoxycinnamate, DEA methoxycinnamate, octocrylene, drometrizole trisiloxane, octyl salicylate, homomenthyl salicylate, octyl dimethyl PABA, TEA salicylate, 4-methyl benzilidene camphor, octyl triazone, terephthalydiene dicamphor sulfonic acid, phenyl benzimidazole sulfonic acid, ethyl PABA, hydroxy methylphenyl benzotriazole, methylene bis-benzotriazoyltetramethylbutylphenol, bis-ethylhexyloxyphenol methoxyphenol triazine, titanium dioxide, zinc oxide, or any derivatives or any combinations thereof. Other useful sunscreen actives include those disclosed in U.S. Pat. No. 5,000,937, which is incorporated herein by reference.

Sunscreen actives of the present invention may be present at up to about 70 percent by weight (wt %), of the total weight of the composition. Preferably, sunscreen actives are present from about 0.05 wt % to about 50 wt %, more preferably about 0.1 wt % to about 30 wt %, and most preferably about 0.5 wt % to about 20 wt %, based on the total weight of the composition. For example, octyl methoxycinnamate is present in an amount about 2 wt % to about 10 wt %, octyl salicylate in an amount about 3 wt % to about 5 wt %, and oxybenzone in an amount about 2 wt % to about 6 wt %.

The preferred sunscreen active is dibenzoylmethane and derivatives thereof. The dibenzoylmethane sunscreen active preferably conforms to the structure:

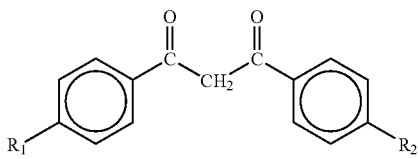

wherein $R_1$ and $R_2$ are alkyl groups having 1–36 carbons.

The dibenzoylmethane sunscreen active includes, but is not limited to, butylmethoxydibenzoylmethane (avobenzone) and 4-isopropyldibenzoylmethane. The most preferred active is butylmethoxydibenzoylmethane. A non-limiting example of the foregoing preferred sunscreen active is available from Roche under the trade name PARSOL 1789.

Preferably, the sunscreen active is dibenzoylmethane or a derivative thereof and is present at up to about 20 wt %, of the total weight of the composition. More preferably, the dibenzoylmethane and/or derivative sunscreen active is present from about 0.05 wt % to about 10 wt %, and most preferably about 0.5 wt % to about 3 wt %, based on the total weight of the composition.

The amount of sunscreen active employed will depend on the level of protection desired. Although not to be construed as limiting, compositions will typically range in level of sunscreen protection factor (SPF) from about 2 up to about 100, preferably from about 2 to about 70, more preferably from about 4 to about 30, and most preferably from about 15 to about 30.

The present composition has an extract of *Kaempferia galanga*. The extract is, preferably, a crystalline solid obtained from the *Kaempferia galanga* plant, also referred to as the Spice Lilly. The extract may be obtained from any part of the plant, such as the leaves, flowers, stem, bark and, most preferably, the root. The extract can include among its constituents the following: borneol, camphene, carene, 3-Carene borneol, 1,8-cineole, cinnamic acid ethyl ester, ethyl p-methoxycinnamate, isoamyl p-methoxycinnamate, n-pentadecane, p-methoxycinnamic acid ethyl ester, p-methoxycinnamic acid methyl ester and/or p-methoxystyrene.

"*Kaempferia galanga* extract" as used herein also includes "synthetic" *Kaempferia galanga* extracts, i.e., various combinations of known *Kaempferia galanga* extract constituents that are combined to substantially mimic the composition and/or activity of a *Kaempferia galanga* extract of natural origin. Such synthetic extracts are included in the term *Kaempferia galanga* extract. The synthetic extracts will have at least one discrete component or active ingredient in common with natural extracts. More preferably, the synthetic extracts will have two or more, three or more, or four or more active ingredients in common with natural extracts. Most preferably, the synthetic extracts will have substantially the same number of active ingredients as the natural extracts. Active ingredients are those that enhance the photostability of sunscreen actives or synergistically enhance UV absorption of a sunscreen-containing composition. The correspondence of the numerical incidence of active ingredients between the synthetic extracts and natural extracts may also be described in terms of "percent commonality." Preferably, the synthetic extract has about 50 percent or more commonality to the chemical composition of a natural extract. In other words, the synthetic extract has about 50 percent or more of the active ingredients found in natural extracts. More preferably, the chemical composition of the synthetic extract has about 70 percent or more commonality to the chemical composition of a natural extract. Optimally, a synthetic extract has about 90 percent or more commonality to the chemical composition of a natural extract. The natural extract is derived, most preferably, from the root of a *Kaempferia galanga* plant.

In one embodiment, the topical sunscreen composition includes a *Kaempferia galanga* extract having less than about 5 wt %, more preferably less than about 4 wt %, of isoamyl p-methoxycinnamate, based upon the total weight of the composition. Most preferably, this embodiment of the topical sunscreen composition is ALSO substantially free of zinc oxide. The term "substantially free of zinc oxide" as used herein means that the topical sunscreen composition has less than about 5 wt %, preferably less than about 4 wt %, and more preferably less than 2 wt % of zinc oxide. Alternatively, when the topical sunscreen composition includes isoamyl p-methoxycinnamate and is not substantially free of zinc oxide, then the topical sunscreen composition also includes dibenzoylmethane and/or a derivative thereof.

Although compositions of the present invention may include from about 0.01 wt % to about 5 wt %, more preferably about 0.5 wt % to about 2 wt %, *Kaempferia galanga* extract, the amount of *Kaempferia galanga* extract is, most preferably, adjusted relative to the amount of sunscreen active. For example, the weight ratio of the extract of *Kaempferia galanga* to the sunscreen active may be from about 0.01:3 to about 3:0.01. This ratio is preferably about 0.01 to 0.5:1, more preferably about 0.05:3, even more preferably about 0.02 to 0.2:1, and most preferably about 1.5:1.

Although an extract of *Kaempferia galanga* is known to be useful as a sunscreen active, the effects observed in the present invention upon combination with other sunscreen actives, particularly dibenzoylmethane and/or derivatives thereof, are surprising and unexpected. First, the extract enhances or improves the photostability of the sunscreen active. The enhancement or improvement in photostability of the sunscreen active lengthens the period of time in which photoprotection by the sunscreen composition is provided. Thus, users of sunscreen compositions having the extract can be protected from sunlight for longer periods of time as compared to sunscreen compositions that do not have the extract. Second, the extract synergistically enhances or increases the level of sun protection typically provided by a sunscreen composition. In other words, the level of sunscreen protection afforded by, for example, butylmethoxy dibenzoylmethane and *Kaempferia galanga* root extract is synergistically greater than the additive effect of these ingredients. This synergistic enhancement permits the use of lower levels of the sunscreen active. Thus, this effect reduces the need for reapplication. A preferred embodiment of the present invention comprises butlylmethoxy dibenzoylmethane, octyl methoxycinnamate and *Kaempferia galanga* root extract.

The present composition may include any cosmetic vehicle known in the art. Suitable vehicles include, but are not limited to, one or more of the following: vegetable oils; esters such as octyl palmitate, isopropyl myristate and isopropyl palmitate; ethers such as dicapryl ether and dimethyl isosorbide; alcohols such as ethanol and isopropanol;

fatty alcohols such as cetyl alcohol, stearyl alcohol and behenyl alcohol; isoparaffins such as isooctane, isododecane and isohexadecane; silicone oils such as dimethicones, cyclic silicones, and polysiloxanes; hydrocarbon oils such as mineral oil, petrolatum, isoeicosane and polyisobutene; polyols such as propylene glycol, ethoxydiglycol, glycerin, butylene glycol, pentylene glycol and hexylene glycol; as well as water, or any combinations of the foregoing.

The amount of cosmetically acceptable vehicle in the present composition will vary considerably based upon product form, but typically will range from about 30 wt % to about 99.95 wt % and preferably about 50 wt % to about 99 wt %, based upon the total weight of the composition.

The present composition may take the form of an emulsion. The emulsion may be, for example, anhydrous, water-in-oil, oil-in-water, water-in-silicone, or multiple emulsions. The present composition, when in emulsion form, preferably has one or more emulsifiers. Emulsifiers that can be used in the composition of the present invention include, but are not limited to, one or more of the following: sorbitan esters dimethicone copolyols; polyglyceryl-3-diisostearate; such as sorbitan monooleate and sorbitan monostearate; glycerol esters such as glycerol monostearate and glycerol monooleate; polyoxyethylene phenols such as polyoxyethylene octyl phenol and polyoxyethylene nonyl phenol; polyoxyethylene ethers such as polyoxyethylene cetyl ether and polyoxyethylene stearyl ether; polyoxyethylene glycol esters; polyoxyethylene sorbitan esters; dimethicone copolyols; polyglyceryl-3-diisostearate; or any combinations thereof. Additional useful emulsifiers and co-emulsifiers are provided in U.S. Pat. No. 5,162,378 (column 4) and U.S. Pat. No. 5,344,665 (Table 1), which are incorporated herein by reference.

When in emulsion form, the present composition preferably has an amount of emulsifier about 0.1 wt % to about 35 wt %, more preferably from about 0.5 to about 25 wt %, and most preferably about 1 wt % to about 12 wt %, based upon the total weight of the composition.

Optionally, the present composition may include one or more of the following ingredients: anesthetics, anti-allergenics, antifungals, antimicrobials, anti-inflammatories, antiseptics, chelating agents, botanical extracts, colorants, depigmenting agents, emollients, exfollients, film formers, fragrances, humectants, insect repellents (especially ethyl butylacetylaminopropionate (IR3535)), lubricants, moisturizers, pharmaceutical agents, preservatives, skin protectants, skin penetration enhancers, stabilizers, surfactants, thickeners, viscosity modifiers, vitamins, or any combinations thereof. Film formers are particularly preferred.

The present compositions may also contain one or more insect repellent actives. Such actives include, but are not limited to, N,N diethyl-m-toluamide (DEET), ethyl butylacetylaminopropionate (IR3535 by Merck Co.), hydroxyethyl isobutyl piperidine carboxylate (1-piperidine carboxylic acid) (Bayer KBR 3023), oil of citronella, soy bean oil, lemon grass oil, geranium/geraniol oil, neem oil and other natural essential oils, p-menthane-3,8-diol, or any mixtures thereof. Other useful actives are disclosed in U.S. Pat. Nos. 5,130,136 and 5,698,209, which patents are incorporated herein by reference. Preferred insect repellent actives are DEET, IR3535, p-menthane-3,8-diol and oil of citronella.

The insect repellent active is present in an amount about 0.05 wt % to about 60 wt %, and preferably about 5 wt % to about 30 wt %, based on the total weight of the composition.

Suitable film formers may include poly(vinyl pyrrolidone/1-triacontene) (Tricontonyl PVP), added at about 3 wt %. This compound contributes film forming and water-proofing qualities to the composition. An example of such a compound is GANEX.RTM. WP 660, a film-forming waterproofing agent distributed by International Specialty Products, Co. Primarily, it is used for high quality waterproofing sunscreen formulations. Other film formers known in the art can be used advantageously in the composition. These include acrylate copolymers, acrylates $C_{12-22}$ alkyl methacrylate copolymer, acrylate/octylacrylamide copolymers, acrylate/VA copolymer, amodimethicone, AMP/acrylate copolymers, behenyl beeswax, behenyl/isostearyl, beeswax, butylated PVP, butyl ester of PVM/MA copolymers, calcium/sodium PVM/MA copolymers, dimethicone, dimethicone copolyol, dimethicone/mercaptopropyl methicone copolymer, dimethicone propylethylenediamine behenate, dimethicolnol ethylcellulose, ethylene/acrylic acid copolymer, ethylene/MA copolymer, ethylene/VA copolymer, fluoro $C_{2-8}$ alkyldimethicone, hexanediol beeswax, $C_{30-38}$ olefin/isopropyl maleate/MA copolymer, hydrogenated styrene/butadiene copolymer, hydroxyethyl ethylcellulose, isobutylene/MA copolymer, laurylmethicone copolyol, methyl methacrylate crosspolymer, methylacryloyl ethyl betaine/acrylates copolymer, microcrystalline wax, nitrocellulose, octadecene/MA copolymer, octadecene/maleic anhydride copolymer, octylacrylamide/acrylate/butylaminoethyl methacrylate copolymer, oxidized polyethylene, perfluoropolymethylisopropyl ether, polyacrylic acid, polyethylene, polymethyl methacrylate, polypropylene, polyquaternium-10, polyquaternium-11, polyquaternium-28, polyquaternium-4, PVM/MA decadiene crosspolymer, PVM/MA copolymer, PVP, PVP/decene copolymer, PVP/eicosene copolymer, PVP/hexadecene copolymer, PVP/MA copolymer, PVP/VA copolymer, silica, silica dimethyl silylate, sodium acrylate/vinyl alcohol copolymer, stearoxy dimethicone, stearoxytrimethylsilane, stearyl alcohol, stearylvinyl ether/MA copolymer, styrene/DVB copolymer, styrene/MA copolymer, tetramethyl tetraphenyl trisiloxane, tricontanyl trimethyl pentaphenyl trisiloxane, trimethylsiloxysilicate, VA/crotonates copolymer, VA/crotonates/vinyl proprionate copolymer, VA/butyl maleate/isobornyl acrylate copolymer, vinyl caprolactam/PVP/dimethylaminoethyl methacrylate copolymer, and vinyldimethicone.

The film former is preferably present in an amount from about 0.5 wt % to about 5 wt %, and more preferably from about 1 wt % to about 5 wt %, based upon the total weight of the composition. More preferably, the film former is present in an amount about 3 wt % of the total weight of the composition.

The composition can be made into any suitable product form. Such product forms include, but are not limited to, an aerosol, balm, cream, gel, lotion, mousse, patch, pomade, pump spray, roll-on, solution, stick or towelette.

EXAMPLE

Solutions of *Kaempferia galanga* extract and butylmethoxy dibenzoyl methane (avobenzone) in diisopropyl adipate were prepared and tested for UVA absorption and photostability. Examples 1 and 2 of the present invention have a weight ratio of 1 to 1 and 0.05 to 3 (*Kaempferia galanga* extract to avobenzone). A Control without the extract was also prepared for comparative purposes.

Photostability was measured using an Optometrics SPF 290 sold by Optometrics U.S.A., Inc. The samples were prepared using the following method:
1. Calculate the sample dosage adjusting for specific gravity;
2. Apply the sample to a substrate; and 3. Scan the sample using Optometrics SPF 290 at a predetermined site to calculate in vitro SPF measurement at that site.

The samples were then irradiated with ultraviolet light from the Optometrics SPF 290 at equivalent spectra to midday summer sunlight at 40° North latitude with a solar zenith of 20° and an ozone thickness of 0.305 cm. The ultraviolet light source is a 125 watt xenon arc lamp with sapphire window. The samples were allowed to remain exposed to the ultraviolet light at the pre-selected position. The samples were scanned every ten minutes for a total of two hours.

Overall photostability of the samples was determined by evaluating changes in the following parameters: i) critical wavelength, ii) erythemal (E) UVA PF, iii) AVG UVA PF, and iv) cumulative absorbance over the two hour period. AVG means average and PF means protection factor.

Results are set forth in Table 1.

TABLE 1

Photostability in Solution

| Parameter | Control 1 (no extract) | Example 1 (1 to 1) | Example 2 (0.05 to 3) |
| --- | --- | --- | --- |
| Δ AVG UVAPF | −91.88% | 18755.00% | 4774.00% |
| Δ E UVAPF | −87.86% | 475.00% | 677.00% |
| Δ Critical Wavelength | −1.845 | −0.61% | −0.50% |
| Δ Cumulative Absorption | −80.65% | 167.00% | 159.00% |

Δ means delta

As is evident from the results above, the change in average UVA protection factor for Examples 1 and 2 of the present invention increased 18,755% and 4,774% respectively, versus an almost 92% decline for the Control. The remainder of the data shows similarly highly surprising results. Thus, a sunscreen-containing composition having galanga extract remains highly photostable as compared to the same composition without the extract.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A method of enhancing the photostability of a sunscreen active in a topical sunscreen composition, the method comprising: introducing into the composition an amount of *Kaempferia galanga* extract sufficient to enhance the photostability of the sunscreen active, wherein the sunscreen active is present in an amount from about 0.05 wt % to about 50 wt %, based upon the total weight of the composition.

2. The method of claim 1, wherein the *Kaempferia galanga* extract is obtained from the part of a plant selected from the group consisting of bark, flower, leaf, root, and stem.

3. The method of claim 2, wherein the *Kaempferia galanga* extract is obtained from the root of the plant.

4. The method of claim 1, wherein the *Kaempferia galanga* extract has at least one active ingredient selected from the group consisting of borneol, camphene, carene, 3-Carene borneol, 1,8-cineole, cinnamic acid ethyl ester, ethyl p-methoxycinnamate, isoamyl p-methoxycinnamate, n-pentadecane, p-methoxycinnamic acid ethyl ester, p-methoxycinnamic acid methyl ester and p-methoxystyrene.

5. The method claim 1, wherein the *Kaempferia galanga* extract is a synthetic *Kaempferia galanga* extract.

6. The method of claim 1, wherein the sunscreen active is selected from the group consisting of dibenzoylmethane or a derivative thereof, oxybenzone, sulisobenzone, dioxybenzone, menthyl anthranilate, para aminobenzoic acid (PABA), octyl methoxycinnamate, DEA methoxycinnamate, octocrylene, drometrizole trisiloxane, octyl salicylate, homomenthyl salicylate, octyl dimethyl PABA, TEA salicylate, 4-methyl benzilidene camphor, octyl triazone, phenyl benzimidazole sulfonic acid, terephthalydiene dicamphor sulfonic acid, ethyl PABA, hydroxy methylphenyl benzotriazole, methylene bis-benzotriazoyltetramethylbutylphenol, bis-ethylhexyloxyphenol methoxyphenol triazine, titanium dioxide, zinc oxide, any derivatives of the foregoing or any combinations of the foregoing.

7. The method of claim 1, wherein the sunscreen active is dibenzoylmethane or a derivative thereof.

8. The method of claim 7, wherein the dibenzoylmethane derivative is butylmethoxydibenzoylmethane.

9. The method of claim 1, wherein the weight ratio of the *Kaempferia galanga* extract to the at least one sunscreen active is about 0.01:3 to about 3:0.01.

10. A method of synergistically enhancing the UV absorbance of a topical sunscreen composition comprising a sunscreen active and a cosmetically acceptable vehicle, the method comprising: introducing into the composition an amount of *Kaempferia galanga* extract sufficient to synergistically enhance UV absorption, wherein the sunscreen active is present in an amount from about 0.05 wt % to about 50 wt %, based upon the total weight of the composition.

11. The method of claim 10, wherein the *Kaempferia galanga* extract is obtained from a *Kaempferia galanga* plant part selected from the group consisting of bark, flower, leaf, root, and stem.

12. The method of claim 10, wherein the *Kaempferia galanga* extract is obtained from a root part of the *Kaempferia galanga* plant.

13. The method of claim 10, wherein the *Kaempferia galanga* extract has at least one active ingredient selected from the group consisting of borneol, camphene, carene, 3-Carene borneol, 1,8-cineole, cinnamic acid ethyl ester, ethyl p-methoxycinnamate, isoamyl p-methoxycinnamate, n-pentadecane, p-methoxycinnamic acid ethyl ester, p-methoxycinnamic acid methyl ester and p-methoxystyrene.

14. The method claim 10, wherein the *Kaempferia galanga* extract is a synthetic *Kaempferia galanga* extract.

15. The method of claim 14, wherein the synthetic *Kaempferia galanga* extract has a chemical composition with about 50 percent or more commonality to a natural *Kaempferia galanga* extract.

16. The method of claim 10, wherein the sunscreen active is at least one of dibenzoylmethane or a derivative thereof, oxybenzone, sulisobenzone, dioxybenzone, menthyl anthranilate, para aminobenzoic acid (PABA), octyl methoxycinnamate, DEA methoxycinnamate, octocrylene, drometrizole trisiloxane, octyl salicylate, homomenthyl salicylate, octyl dimethyl PABA, TEA salicylate, 4-methyl benzilidene camphor, phenyl benzimidazole sulfonic acid, octyl triazone, terephthalydiene dicamphor sulfonic acid, ethyl PABA, hydroxy methylphenyl benzotriazole, methylene bis-benzotriazoyltetramethylbutylphenol, bis-ethylhexyloxyphenol methoxyphenol triazine, titanium dioxide, zinc oxide, any derivatives of the foregoing or any combinations of the foregoing.

17. The method of claim 10, wherein the sunscreen active is dibenzoylmethane or a derivative thereof.

18. The method of claim 17, wherein the dibenzoylmethane is butylmethoxydibenzoylmethane.

19. The method of claim 10, wherein the weight ratio of *Kaempferia galanga* extract to the at least one sunscreen active is about 0.01 to 0.05:1.

20. A topical sunscreen composition, comprising:
from about 0.05 wt % to about 50 wt % of a sunscreen active and
a *Kaempferia galanga* extract.

21. The composition of claim 20, wherein the *Kaempferia galanga* extract is obtained from a *Kaempferia galanga* plant part selected from the group consisting of bark, flower, leaf, root, and stem.

22. The composition of claim 21, wherein the *Kaempferia galanga* extract is the extract from the root of a *Kaempferia galanga* plant.

23. The composition of claim 20, wherein the sunscreen active comprises one or more dibenzoylmethane, oxybenzone, sulisobenzone, dioxybenzone, menthyl anthranilate, para aminobenzoic acid (PABA), octyl methoxycinnamate, DEA methoxycinnamate, octocrylene, drometrizole trisiloxane, octyl salicylate, homomenthyl salicylate, octyl dimethyl PABA, TEA salicylate, 4-methyl benzilidene camphor, octyl triazone, terephthalydiene dicamphor sulfonic acid, phenyl benzimidazole sulfonic acid, ethyl PABA, hydroxy methylphenyl benzotriazole, methylene bis-benzotriazoyltetramethylbutylphenol, bis-ethylhexyloxyphenol methoxyphenol triazine, titanium dioxide, zinc oxide, or any derivatives thereof.

24. The composition of claim 20, wherein the sunscreen active is dibenzoylmethane or a derivative thereof.

25. The composition of claim 20, wherein the sunscreen active is butylmethoxydibenzoylmethane.

26. The composition of claim 20, wherein the *Kaempferia galanga* extract is present in an amount sufficient to enhance the photostability of the sunscreen active.

27. The composition of claim 26, wherein the *Kaempferia galanga* extract is present in an amount sufficient to synergistically enhance UV absorbance of the composition.

28. The composition of claim 20, wherein the weight ratio of the *Kaempferia galanga* extract to the sunscreen active is from about 0.01:3 to about 3:0.01.

29. The composition of claim 20, further comprising a film former.

30. The composition of claim 29, wherein the film former is present in an amount about 0.5 wt % to about 5 wt % based on the total weight of the composition.

31. The composition of claim 20, further comprising an insect repellent selected from the group consisting of N,N diethyl-m-toluamide, ethyl butylacetylaminopropionate, hydroxyethyl isobutyl piperidine carboxylate, oil of citronella, soy bean oil, lemon grass oil, geranium/geraniol oil, neem oil, p-menthane-3,8-diol, and any combinations thereof.

32. The composition of claim 20, wherein the composition is in the form of an aerosol, balm, cream, gel, lotion, mousse, patch, pomade, pump spray, roll-on, solution, stick or towelette.

33. The composition of claim 20, wherein the sunscreen active is butylmethoxydibenzoylmethane, and the weight ratio of the *Kaempferia galanga* extract to butylmethoxydibenzoylmethane is about 0.01:3 to about 3:0.01.

34. The composition of claim 20, wherein the sunscreen active is butylmethoxydibenzoylmethane, and the weight ratio of the *Kaempferia galanga* extract to the at least one sunscreen active is about 0.01 to 0.5:1.

35. The composition of claim 20, wherein the *Kaempferia galanga* extract is a synthetic *Kaempferia galanga* extract.

36. The composition of claim 20, wherein the synthetic *Kaempferia galanga* extract has a chemical composition with about 50 percent or more commonality to a natural *Kaempferia galanga* extract.

37. The composition of claim 35, wherein the synthetic *Kaempferia galanga* extract has at least one active ingredient selected from the list consisting of borneol, camphene, carene, 3-Carene borneol, 1,8-cineole, cinnamic acid ethyl ester, ethyl p-methoxycinnamate, isoamyl p-methoxycinnamate, n-pentadecane, p-methoxycinnamic acid ethyl ester, p-methoxycinnamic acid methyl ester, and p-methoxystyrene.

38. The method of claim 10, wherein the synthetic *Kaempferia galanga* extract has four or more active ingredients in common with a natural *Kaempferia galanga* extract.

39. The method of claim 10, wherein the synthetic *Kaempferia galanga* extract has substantially the same number of active ingredients as a natural *Kaempferia galanga* extract.

* * * * *